United States Patent [19]

Landsiedel et al.

[11] Patent Number: 4,968,455
[45] Date of Patent: Nov. 6, 1990

[54] TRIS(TRIORGANOTIN) ESTERS OF TRIMERIC FATTY ACIDS

[75] Inventors: Horst Landsiedel, Froendenberg; Hans Plum, Hamm, both of Fed. Rep. of Germany

[73] Assignee: Schering Aktiengesellschaft, Berlin and Bergkamen, Fed. Rep. of Germany

[21] Appl. No.: 783,464

[22] Filed: Oct. 3, 1985

[30] Foreign Application Priority Data

Oct. 11, 1984 [DE] Fed. Rep. of Germany ....... 3437316

[51] Int. Cl.$^5$ ................................................ C11C 1/00
[52] U.S. Cl. .................................... 260/407; 260/414; 514/493
[58] Field of Search .............................. 260/414, 407

[56] References Cited

U.S. PATENT DOCUMENTS

| 3,167,473 | 1/1965 | Leebrick | 167/38.6 |
| 3,214,453 | 10/1965 | Stern | 260/429.7 |
| 4,039,494 | 8/1977 | Drisko | 260/22 A |
| 4,373,953 | 2/1983 | Deinet et al. | 514/493 |
| 4,488,998 | 12/1984 | Miller et al. | 260/414 |

FOREIGN PATENT DOCUMENTS

| 0741814 | 8/1966 | Canada . |
| 1280852 | 10/1968 | Fed. Rep. of Germany . |
| 1443938 | 6/1969 | Fed. Rep. of Germany . |
| 2118702 | 11/1974 | Fed. Rep. of Germany . |
| 1308389 | 2/1973 | United Kingdom . |
| 1352476 | 5/1974 | United Kingdom . |

OTHER PUBLICATIONS

Chem. Reviews, vol. 60 (1960) p. 522.
Craig, Organometallic Compounds in the Environment, Longman, 1986.

Primary Examiner—Charles F. Warren
Attorney, Agent, or Firm—Curtis, Morris & Safford

[57] ABSTRACT

Tris(triorganotin) esters of trimeric fatty acids wherein the groups which are organically combined with the tin atom are the same or different and are linear or branched alkyl having from 3 to 6 carbon atoms, cyclohexyl, or phenyl, and biocidal agents containing these compounds as an active ingredient.

5 Claims, No Drawings

TRIS(TRIORGANOTIN) ESTERS OF TRIMERIC FATTY ACIDS

The present invention relates to certain tris(triorganotin) esters of trimeric fatty acids, to biocidal agents containing such esters, and to methods for combating organisms with such esters.

It is known that triorganotin compounds possess a good biocidal activity which extends to bacteria, fungi, algae and certain marine organisms such as balanids and sabellariids.

The biocidal activity of triorganotin compounds of the type $R_3SnX$, where R is alkyl, cyclohexyl, or phenyl and X an anionic group, is determined primarily by the chain length of the hydrocarbon groups attached to the tin atom. (International Tin Research Institute, Publication No. 599, 1979; Dr. Bokranz and Dr. Plum, Advances in Chemical Research, vol. 16, No. 3-4,P. 377.) Optimum activity is achieved when the total number of the carbon atoms attached to the tin atom in the alkyltin compounds ranges from 9 to 12, that is, with tripropyl- and tributyl- tin compounds. The triphenyl- and tricyclohexyltin compounds exhibit comparable biocidal activity.

The anionic group X generally has no influence on the biocidal activity of the triorganic compounds. Efficacy is determined by the trialkyltin content. Tributyl (TBT) esters of long chain acids, for example, tributyltin naphthenate (TBTN) or tributyltin linoleate (TBTL), whose tin content is only about half of that of tributyltin oxide (TBTO), therefore must be used in amounts roughly double those of TBTO to obtain the same biocidal activity.

The anionic group X does, however, influence the physical properties of the triorganotin compounds. For example, tributyltin oxide and tributyltin chloride are low viscosity liquids, tributyltin abietate and tributyltin phosphate are medium-to-high viscosity liquids, and tributyltin fluoride is a solid. The triorganotin compound used most widely for the protection of materials is tri-n-butyltin oxide. When the oxygen in this compound is replaced by other anionic groups (for example, acid groups of organic or inorganic acids), the products obtained usually have lower water solubility, lower volatility, and higher thermal stability.

For example, tributyltin naphthenate and tributyltin linoleate have properties which are considerably better in this respect than tributyltin oxide.

The object of the present invention thus is to provide triorganotin compounds which possess significantly better properties with respect to water solubility, evaporation loss, and thermal stability, than the tributyltin esters of naphthenic acid or linseed oil fatty acid which have already found commercial uses.

It has unexpectedly been found that the tris(triorganotin) esters of trimeric fatty acids incorporate substantial improvements in the aforementioned properties which are of decisive importance so far as their use as active biocidal substances is concerned.

The invention particularly relates to tris(triorganotin) esters of trimeric fatty acids in which the groups which are organically attached to the tin atom may be linear or branched alkyl having from 3 to 6 carbon atoms, cyclohexyl, or phenyl. These groups may be the same or different. Thus, the compounds of the invention have the formula $(R_3SnO)_3X$, where X is a trimeric fatty acid acyl group.

The tris(tributyltin) esters of trimeric fatty acids, and particularly of trimeric fatty acids obtained from fatty acids having 18 carbon atoms, such as tall oil fatty acid, are preferred.

The invention particularly relates to biocidal agents containing these compounds as active ingredients, and to the use of these compounds and agents in the control of bacteria, fungi, algae, and marine growth organisms, and particularly wood damaging organisms.

"Trimeric fatty acids" are the polymolecular fractions obtained by well-known prior art processes (e.g. published German patent applications Nos. 14 43 938 and 14 43 968, and German patents Nos. 21 18 702 and 12 80 852) for the polymerization of unsaturated natural or synthetic monobasic aliphatic fatty acids having from 16 to 22, and preferably 18, carbon atoms in the alkyl group. Illustrative of suitable fatty acids are natural higher fatty acids such as linoleic acid, oleic acid, stearic acid, soybean oil fatty acid, and particularly tall oil fatty acid. The "trimeric fatty acids" essentially consist of trimerized acids in the form of different isomers, minor amounts of dicarboxylic acids and oligomeric fatty acids, and traces of monocarboxylic acids.

As is known, the composition of trimeric acids depends on a number of factors, such as the type and composition of the starting fatty acid, the reaction conditions, the type of catalyst, and the distillation conditions in the separation of dimeric acid. (Leonard, E. C., "The Dimer Acids," Humko Sheffield Chemicals, Conn., 1975.)

After dimeric acid has been distilled off, the trimeric fatty acid obtained in the commercial production of dimeric fatty acid contains between about 70 and 90 weight percent of trimeric and oligomeric acids.

The biocides used in practice for the preservation of materials are expected to be effective against a variety of microorganisms and to provide long lasting protection against attack.

The compounds according to the present invention can particularly be used for the protection of wood since by their use protection against attack by those bacteria and fungi which discolor wood, as well as an inhibition of the decomposition of wood by fungi, can be achieved. Bacteria do not effect the decomposition of wood but they can favor an attack by fungi.

The compounds according to the present invention are used in the form of solutions, optionally containing auxiliaries and coloring agents, and are suitably applied to wood by painting, spraying, or immersion, for example.

Further, the active agents according to the invention can be used for the biocidal treatment of textiles, synthetic resins, building materials, and in coatings, in which case they are suitably used in the form of preparations such as solutions, emulsions, dispersions with and without binders, or can be used with solid carriers or diluents, optionally with the addition of surface-active agents, agents causing adherence, emulsifying agents, or dispersing auxiliaries.

The concentration of active ingredient generally is in the range from 0.05 to 50.0 percent by weight of the composition and is determined by the nature of the use and the absorptive capacity of the substrate.

For the protection of wood, solutions of the compounds of the present invention in gasoline fractions are preferred, with the optional addition of agents which increase penetration, binders—especially alkyd resins—, or other solvents, in concentrations from 0.05 to 5.0 percent by weight and are applied by painting or the like in amounts such as provide 50 to 400 g of solution of active agent per square meter of wood surface.

With the use of suitable emulsifiers, the compounds according to the present invention can be used to produce water-dilutable formulations which also can be used for the protection of wood, e.g. by painting, immersion, or the like, in the form of emulsions containing from 0.5 to 3.0 percent of active ingredient. For the protection of wood construction materials, the compounds of the present invention can be combined, in the form of highly concentrated solutions or formulations with an emulsifier, with a binder or adhering agent in an amount from 0.1 to 2.0 percent by weight of the active ingredient.

Emulsifiable concentrates can be prepared by solution of the active ingredient in an inert organic solvent such as alcohols, ketones, cyclohexanone, xylene or higher boiling aromatic compounds, or hydrocarbons such as gasoline fractions, with the addition of one or more emulsifiers. When the active ingredients are liquid, the amount of solvent can be reduced or omitted entirely.

Suitable emulsifiers are, for example, alkylaryl sulfonates, e.g. Ca-dodecylbenzene sulfonate, and particularly non-ionic emulsifiers such as fatty acid polyglycol esters, alkylaryl polyglycol ethers, fatty alcohol polyglycol ethers, propylene oxide-ethylene oxide-condensation products, and alkyl polyglycol ethers.

For the protection of textiles, such as woven cottons, against undesirable microorganisms, the compounds can be applied in the form of a solution, e.g. in ethanol, xylene, or a ketone, having a concentration of active ingredient from 0.05 to 3.0 percent by weight, by means of spraying or immersion. Waterproofing agents can optionally be added to such solutions.

For broadening the activity spectrum, in order to obtain special effects against particular microorganisms or for insecticidal treatment, the compounds of the present invention can be combined with other active ingredients such as the following, which are given as exemplary only and are not an exhaustive listing: 3-iodo-2-propynyl-butyl-carbamate; copper naphthenate; copper-8-oxiquinoline; N-cyclohexyl-N-methoxy-2,5-dimethyl-furan-3-carboxylic acid-amide; N,N'-dimethyl-N-phenyl-N'-fluorodichloromethyl-thiosulfonyl-diamide; benzimidazole-2-carbaminic acid-methyl ester; N-tri-chloromethylthio-phthalimide; gamma-hexachlorocyclohexane; and permethrin.

The permanence of the material preservation is influenced by a number of factors. For example, a certain solubility of the biocide in water can have an adverse effect on permanent protection since leaching of the treated material can occur and exposure to moisture (for example, rain or dew), which reduces the concentration of biocidal active ingredients. The water solubility of the tristributyltin esters of trimeric fatty acids according to the invention is only about one-fourth that of the tributyltin esters known in the art (see Table 1 below).

An important factor affecting the permanence of the biocidal activity is the thermal stability of the active ingredients. Materials, for example, dark-stained wood, which are treated with a biocide and are subject to weathering can reach temperatures ranging from 60° to 70° C. when exposed to the sun's rays for an extended period of time.

Under such stress, thermally unstable products decompose and thus lose their biocidal activity. Surprisingly, tris(tributyltin) esters of trimeric fatty acids possess significantly better thermal stability than the tributyltin esters used up to now (as will be apparent from Table 2 below).

In addition to thermal stability, an important factor in the long range protection provided by biocidal products is their evaporation behavior under thermal stresses. High rates of release of biocides from treated materials may result in unjustified pollution of the environment and also reduce the long term activity.

In this respect, the inventive tris(tributyltin) esters of trimeric fatty acids possess very good properties. The release rates on exposure to a temperature of 65° C. for seven days are only about 15 to 20 percent of those of the tributyltin esters used up to now. (See Table 3 below.)

In tests run with a thermobalance, tris(tributyltin) esters of trimeric fatty acids showed a weight loss that was lower and set in much later than the weight loss to which the tributyltin compounds used up to now are subject. (See Table 3 below.)

The use of biocidal agents incorporating the inventive tris(triorganotin) esters of trimeric fatty acids thus results in less pollution since both the release rates and the concentration in which the biocide is used are reduced, the latter reduction being made possible by the long term stability of the esters.

Thus, when wood is coated with materials containing a compound of the invention as an active ingredient, the concentration of the compound in the air above the treated wood is lower than in the case of a coating with a tributyltin ester as used up to now. (See Table 4 below.)

A further advantage of the compounds of the invention is that they cause less skin irritation than prior art tributyltin compounds.

A better understanding of the present invention and of its many advantages will be had by referring to the following examples, given by way of illustration.

The reaction of the trimeric fatty acid with an amount of triorganotin compound equivalent to the acid number is carried out as follows:

EXAMPLE 1

Preparation of a tris(tributyltin) ester of trimeric fatty acid 570.7 g of trimeric fatty acid, obtained by polymerization of tall oil fatty acid, with an acid number of 197 and a content of trimeric or oligomeric fatty acids of 72 wt. %, 598.0 g of TBTO, and 1,178.0 g of xylene.

The components are heated to the boiling point of xylene and the water of reaction is simultaneously distilled off azeotropically through a bridge. The amount of xylene is such that a 50 wt. % solution of the tributyltin ester of the trimeric fatty acid is obtained. (The 100% product is very highly viscous and difficult to handle.) Completion of the conversion is verified by measuring the amount of water formed. The product is a yellow, clear solution with a tin content of 9.8 wt. %, which corresponds to a tin content of 19.6 wt. % for the 100% product.

EXAMPLE 2

Preparation of a tris(tributyltin) ester of trimeric fatty acid 604 g of trimeric fatty acid, obtained by the polymerization of tall oil fatty acid, with an acid number of 186 and a content of trimeric or oligomeric fatty acids of 87 wt. %,
598 g of TBTO, and
1,211 g of xylene.

The same procedure is followed as in Example 1. A yellow, clear solution with a tin content of 9.3 wt. % is obtained, which corresponds to a tin content of 18.6 wt. % for the 100% product.

EXAMPLE 3

Preparation of a tris(tripropyltin) ester of trimeric fatty acid 590 g of trimeric fatty acid, obtained by the polymerization of tall oil fatty acid, with an acid number of 190 and a content of trimeric or oligomeric fatty acids of 84%,
512 g of tripropyltin oxide, and
1,111 g of xylene.

The same procedure is followed as in Example 1. A yellow, clear solution with a tin content of 10.6 wt. % is obtained, which corresponds to a tin content of 21.2 wt. % for the 100% product.

EXAMPLE 4

Preparation of a tris(triphenyltin) ester of trimeric fatty acid 590 g of trimeric fatty acid, obtained by the polymerization of tall oil fatty acid, with an acid number of 190 and a content of trimeric or oligomeric fatty acids of 84%,
716 g of triphenyltin oxide, and
1,315 g of xylene.

The same procedure is followed as in Example 1. A yellow, clear solution with a tin content of 8.9 wt. % is obtained, which corresponds to a tin content of 17.8 wt. % for the 100% product.

EXAMPLE 5

Preparation of a tris(tricyclohexyltin) ester of trimeric fatty acid 295 g of trimeric fatty acid, obtained by the polymerization of tall oil fatty acid, with an acid number of 190 and a content of trimeric or oligomeric fatty acids of 84%,
385 g of tricyclohexyltin hydroxide, and
690 g of xylene.

The same procedure is followed as in Example 1. A yellow, clear solution with a tin content of 8.7 wt. % is obtained, which corresponds to a tin content of 17.4 wt. % for the 100% product.

The products from Examples 1 and 2 were tested for the following properties. The data so obtained are compared with those obtained with TBTO or the TBT esters of naphthenic acid (TBTN) or linseed oil fatty acid (TBTL).

1. Solubility of tap water 1 g of the substance to be tested was mixed in a beaker with 1 liter of tap water by stirring for one week. After settling and decanting, the organotin compounds dissolved in the water were extracted with chloroform. The tin concentrations were determined by atomic absorption spectroscopy.

TABLE 1

| Product | Water solubility (mg/liter of water) |
|---|---|
| TBTO | 24.0 |
| TBTN | 1.5 |
| TBTL | 1.3 |
| Product of Example 1 (based on 100%) | 0.3 |
| Product of Example 2 (based on 100%) | 0.3 |

2. Thermal stability

After prior methylation, the content of tributyltin compounds after a one hour treatment at 180° C. in open glass vessels was determined by gas chromatography.

TABLE 2

| Product | Tributyltin content after 1 hour at 180° C. (wt. %) |
|---|---|
| TBTO | Not determinable (98% weight loss) |
| TBTN | 81.7 |
| TBTL | 86.1 |
| Product of Example 1 (based on 100%) | 92.7 |
| Product of Example 2 (based on 100%) | 93.2 |

3. Evaporation behavior

Weight losses were determined after one week storage in a circulating-air dryer at 65° C. and tests with a thermobalance (onset of weight loss, and weight loss at 350° C.) were performed.

The exact initial weight of the specimens (about 2 g) in glass Petri dishes (about 10 cm in diameter) is determined and the weight loss after treatment is determined by reweighing.

TABLE 3

| Product | Weight loss after 7 days at 65° C. (%) | Thermobalance Onset of weight loss (°C.) | Thermobalance Weight loss at 350° C. (%) |
|---|---|---|---|
| TBTO | 27.3 | 75 | 80 |
| TBTN | 1.7 | 140 | 66 |
| TBTL | 1.3 | 130 | 59 |
| Product of Example 1 (based on 100%) | 0.3 | 175 | 34 |
| Product of Example 2 (based on 100%) | 0.2 | 180 | 33 |

4. Release rates

To determine the rates of release from treated wood reported in Table 4, pine boards 2 cm thick were coated on one side with the test solution and, after an evaporation time of three days at room temperature, stored in a closed plastic box from which air was removed continuously by suction. The escaping tributyltin compounds were absorbed in a small tube filled with activated charcoal, in which the tin content was then determined.

The volume of the box was 0.2 m³, the surface area of the coated boards 0.2 m², and the rate of air replacement twice per hour.

Each of the coating solutions contained 10 wt. % of alkyd resin, dissolved in "Crystal Oil 60" (white spirit, a gasoline fraction boiling in the range from 180° C. to 210° C.), with additions of TBTL, TBTN, and the products from Examples 1 and 2, in equal amounts, based on tin content.

The tin concentration in the air after various periods of time are given in Table 4. The individual testing periods were two weeks.

TABLE 4

Tin concentrations in the air above the coated boards (micrograms/m³)

| TBT Compound in solution (wt. %) | Number of weeks after coating | | |
|---|---|---|---|
| | 2 | 14 | 26 |
| 3.0 TBTN | 2.02 | 0.55 | 0.44 |
| 3.0 TBTL | 1.84 | 0.49 | 0.41 |
| 6.5 Product of Ex. 1 | 1.04 | 0.28 | 0.22 |
| 6.6 Product of Ex. 2 | 0.98 | 0.26 | 0.21 |

5. Biocidal activity

For comparison of biocidal activity (Table 5), filter paper disks (5.5 cm in diameter) were impregnated with graded concentrations of the active substances in ethanol, air dried, and then placed in Petri dishes on nutrient agar inoculated with bacteria suspensions or spore suspensions of test fungi, and incubated for two days at 37° C. (bacteria) or three weeks at 30° C. (fungi). The zones of inhibition about the specimens, i.e. the areas of the annular zones of inhibited growth surrounding the circumference of the treated paper disks, were then determined in cm².

The biocidal activity of these products, based on tin content, is equal to that of the TBT esters of naphthenic acid (TBTN) or linseed oil fatty acid (TBTL).

The microorganisms used in the test were *Lenzites trabea, Coniophora puteana, Polystictus versicolor, Poria monticolor*, and *Chaetomium globosum*.

TABLE 5

Overlay test: Zones of inhibition about the specimens, in cm²

| Impregnating solution = (wt. %) | wt. % tin | FUNGI | | | | |
|---|---|---|---|---|---|---|
| | | Lenz. trab. | Con. put. | Polyst. vers. | Por. mont. | Chaet. glob. |
| TBTL | | | | | | |
| 2.0 | 0.40 | 14 | 14 | 8 | 18 | 16 |
| 1.2 | 0.24 | 12 | 14 | 5 | 12 | 16 |
| 0.8 | 0.16 | 12 | 10 | 4 | 8 | 12 |
| 0.5 | 0.10 | 7 | 6 | 3 | 6 | 10 |
| TBTN | | | | | | |
| 2.0 | 0.40 | 14 | 14 | 8 | 16 | 18 |
| 1.2 | 0.24 | 14 | 12 | 5 | 10 | 16 |
| 0.8 | 0.16 | 12 | 10 | 5 | 10 | 12 |
| 0.5 | 0.10 | 8 | 6 | 3 | 6 | 10 |
| Product of Ex. 1 | | | | | | |
| 4.1 | 0.40 | 14 | 14 | 8 | 14 | 14 |
| 2.45 | 0.24 | 12 | 12 | 4 | 10 | 12 |
| 1.65 | 0.16 | 10 | 9 | 4 | 8 | 12 |
| 1.0 | 0.10 | 7 | 6 | 3 | 5 | 8 |
| Product of Ex. 2 | | | | | | |
| 4.3 | 0.40 | 14 | 14 | 8 | 14 | 14 |
| 2.6 | 0.24 | 10 | 12 | 5 | 10 | 12 |
| 1.7 | 0.16 | 10 | 10 | 4 | 7 | 10 |
| 1.1 | 0.10 | 8 | 6 | 2 | 6 | 7 |
| Controls | | 0 | 0 | 0 | 0 | 0 |

| Impregnating solution = | wt. % | BACTERIA | | |
|---|---|---|---|---|
| | | Bacillus | Bacillus | Proteus |

TABLE 5-continued

Overlay test: Zones of inhibition about the specimens, in cm²

| (wt. %) | tin | mesentericus | subtilis | vulgaris |
|---|---|---|---|---|
| TBTO | | | | |
| 1.0 | 0.40 | 20 | 20 | 12 |
| 0.6 | 0.24 | 14 | 18 | 9 |
| 0.4 | 0.16 | 8 | 13 | 6 |
| 0.25 | 0.10 | 5 | 6 | 3 |
| TBTL | | | | |
| 2.0 | 0.40 | 11 | 13 | 10 |
| 1.2 | 0.24 | 6 | 8 | 7 |
| 0.8 | 0.16 | 5 | 3 | 3 |
| 0.5 | 0.10 | 3 | 3 | 2 |
| TBTN | | | | |
| 2.0 | 0.40 | 10 | 12 | 10 |
| 1.2 | 0.24 | 6 | 7 | 6 |
| 0.8 | 0.16 | 6 | 6 | 4 |
| 0.5 | 0.10 | 3 | 3 | 2 |
| Product of Ex. 1 | | | | |
| 4.1 | 0.40 | 10 | 12 | 9 |
| 2.45 | 0.24 | 5 | 6 | 6 |
| 1.65 | 0.16 | 5 | 5 | 3 |
| 1.0 | 0.10 | 3 | 3 | 3 |
| Product of Ex. 2 | | | | |
| 4.3 | 0.40 | 10 | 11 | 9 |
| 2.6 | 0.24 | 6 | 7 | 6 |
| 1.7 | 0.16 | 5 | 4 | 2 |
| 1.1 | 0.10 | 2 | 3 | 2 |
| Control | | 0 | 0 | 0 |

(completely cover with growth)

The following examples show formulations containing the compounds of the present invention as active ingredients:

EXAMPLE 6

A colorless formulation containing a small amount of binder and which shows good penetrating power and is particularly suitable for the treatment of wood used in construction has the following composition, wherein the components are given in parts by weight:
2.5 parts of the reaction product of Example 1;
5 parts of diethylene glycol monobutyl ether;
10 parts of alkyl resin (about 33 percent of phthalate resin and about 67 percent of triglycerides of plant fatty acids);
82.5 parts of white spirit ("Crystal Oil 60").

EXAMPLE 7

A colored glaze for wood, suitable for painting dimensioned wood constructions such as window frames, doors, and the like, comprises, in parts by weight:
2.0 parts of the reaction product of Example 2;
40 parts of the oily alkyd resin of Example 1;
0.5 part of a drying agent (Co-,Mn-,Pb-salts);
0.5 part of an anti-settling agent;
9.2 parts of a red iron oxide paste;
0.8 part of black iron oxide paste;
6 parts of diethylene glycol monobutyl ether;
39.8 parts of white spirit ("Crystal Oil 60").

EXAMPLE 8

A water-dilutable combination containing active ingredient, comprising, in parts by weight:
20 parts of the reaction product of Example 3;
5 parts of N,N'-dimethyl-N-phenyl-N'-fluorodichloromethyl-thiosulfonyl-diamide;
75 parts of non-ionic emulsifier
can be diluted over a wide region (1:5 to 1:50) with water to provide stable emulsions for the spraying or immersion of, for example, freshly felled wood. The undiluted formulation is suitably added in amounts of 0.2–3.0 percent by weight to aqueous coating systems, for example, dispersions of acrylate resins, to impart biocidal properties thereto.

We claim:

1. A tris(triorganotin) ester of a trimeric fatty acid $(R_3SnO)_3X$, wherein R is the same or different linear or branched alkyl having from 3 to 6 carbon atoms, cyclohexyl, or phenyl, and X is trimeric fatty acid acyl.

2. A tris(triorganotin) ester as in claim 1, wherein R is butyl.

3. A tris(triorganotin) ester as in claim 1, wherein said trimeric fatty acid is obtained by trimerizing a fatty acid having 18 carbon atoms.

4. A tris(triorganotin) ester as in claim 1, wherein said trimeric fatty acid is trimerized tall oil fatty acid.

5. A biocidal agent comprising a tris(triorganotin) ester as in claim 1 together with a carrier therefor.

* * * * *